United States Patent [19]

Suzuki et al.

[11] 4,279,924

[45] Jul. 21, 1981

[54] MIXTURE OF STEREOISOMERS OF α-CYANO-3-(4-HALOGENOPHENOXY)BENZYL 2-(4-CHLOROPHENYL)ISOVALERATE, A PROCESS FOR PRODUCING THE SAME, AND A COMPOSITION CONTAINING THE SAME

[75] Inventors: Yukio Suzuki, Toyonaka; Kiyoshi Kasamatsu, Takarazuka; Kohichi Aketa, Kawanishi, all of Japan

[73] Assignee: Sumitomo Chemical Company, Limited, Osaka, Japan

[21] Appl. No.: 118,887

[22] Filed: Feb. 6, 1980

[30] Foreign Application Priority Data

Feb. 6, 1979 [JP] Japan ................... 54/13034

[51] Int. Cl.³ .................... A01N 37/34; C07C 121/75
[52] U.S. Cl. ................... 424/304; 260/465 D
[58] Field of Search ............... 260/465 D; 424/304

[56] References Cited

U.S. PATENT DOCUMENTS

| 4,133,826 | 1/1979 | Warnant et al. | 260/465 D |
| 4,176,195 | 11/1979 | Stoutamire | 424/304 |

FOREIGN PATENT DOCUMENTS

| 853411 | 10/1977 | Belgium . |
| 857859 | 12/1977 | Belgium . |
| 0002289 | 6/1979 | European Pat. Off. . |
| 54-103831 | 8/1979 | Japan . |
| 54-103833 | 8/1979 | Japan . |
| 7806273 | 12/1978 | Netherlands . |
| 7807368 | 1/1979 | Netherlands . |
| 2013206 | 8/1979 | United Kingdom . |

*Primary Examiner*—Dolph H. Torrence
*Attorney, Agent, or Firm*—Sughrue, Rothwell, Mion, Zinn and Macpeak

[57] ABSTRACT

A mixture of stereoisomers of an α-cyano-3-(4-halogenophenoxy)benzyl 2-(4-chlorophenyl)isovalerate, which consists substantially of or is rich in an enantiomer pair of an (S)-α-cyano-3-(4-halogenophenoxy)benzyl (S)-2-(4-chlorophenyl)isovalerate and an (R)-α-cyano-3-(4-halogenophenoxy)benzyl (R)-2-(4-chlorophenyl)isovalerate; a process for preparing the same; and an insecticidal and/or acaricidal composition containing the same.

14 Claims, No Drawings

MIXTURE OF STEREOISOMERS OF α-CYANO-3-(4-HALOGENOPHENOXY)BENZYL 2-(4-CHLOROPHENYL)ISOVALERATE, A PROCESS FOR PRODUCING THE SAME, AND A COMPOSITION CONTAINING THE SAME

BACKGROUND OF THE INVENTION

1. Field of the Invention

This invention relates to a mixture of stereoisomers with higher activity of an α-cyano-3-(4-halogenophenoxy) benzyl 2-(4-chlorophenyl)isovalerate of the formula (I):

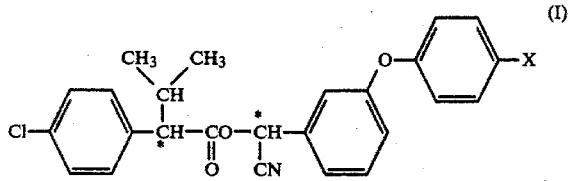

wherein X is a fluorine atom, a chlorine atom or a bromine atom, and * indicates an asymmetric carbon atom, which contains at least 60% of an enantiomer pair of a compound of the formula (I) having an (S)-configuration on both the acid and alcohol moieties and its enantiomer, or which consists substantially of the enantiomer pair, a process for preparing the same, and an insecticidal and/or acaricidal composition containing the same.

2. Description of the Prior Art

α-Cyano-3-(4-hologenophenoxy)benzyl 2-(4-chlorophenyl) isovalerates of the formula (I) are compounds useful as insecticides and acaricides. These esters have one asymmetric carbon atom on each of the acid and alcohol moieties. An ester provided by the conventional method is a mixture comprising substantially equal amounts of four isomers.

These optical isomers are hereunder referred to as shown in Table 1 below.

TABLE 1

| Alcohol Moiety | Abbreviations for Optical Isomers | | |
| --- | --- | --- | --- |
| | Acid Moiety | | |
| | (S)-Configuration | Racemic | (R)-Configuration |
| (S)-Configuration | Aα-Isomer | α-Isomer | Bα-Isomer |
| Racemic | A-Isomer | "Racemate" | B-Isomer |
| (R)-Configuration | Aβ-Isomer | β-Isomer | Bβ-Isomer |

The enantiomer pair of the Aα-isomer and the Bβ-isomer is referred to as a Y-isomer, and the enantiomer pair of the Aβ-isomer and the Bα-isomer as an X-isomer.

The Aα-isomer, Bα-isomer, Aβ-isomer and Bβ-isomer exhibit greatly differing insecticidal and/or acaricidal activity, and the Aα-isomer, i.e., an ester having an (S)-configuration on both the acid and alcohol moieties, has the highest activity. An ester, "racemate", of the formula (I) synthesized from a conventional starting racemate contains almost equal amounts of all of the isomers, and therefore its activity is only about a quarter of the activity of the Aα-isomer. For this reason, the method of producing an ester of the formula (I) with a high content of Aα-isomer would be greatly advantageous in practice.

Possible means for achieving this purpose include one for obtaining an ester (A-isomer) having an (S)-configuration on the acid moiety (i.e., a mixture of the Aα-isomer and the Aβ-isomer), an ester having an (S)-configuration on the alcohol moiety (i.e., a mixture of the Aα-isomer and the Bα-isomer), or the Aα-isomer per se. However, none of these techniques can be performed without an optically active starting material that is generally obtained by complicated procedures, i.e., optical resolution.

Combinations of the Aα-isomer and the Bβ-isomer, and the Aβ-isomer and the Bα-isomer are each in a relationship of enantiomer pair. The other combinations of isomers are diastereomers for one another. Therefore, if some means were devised that can provide a Y-isomer, it is expected that the insecticidal and/or acaricidal activity of an ester of the formula (I) in the racemic form obtainable by the conventional method will be almost doubled because the Y-isomer contains as much as 50% of an Aα-isomer.

Heretofore, diastereomers have been isolated by chromatographic techniques such as column chromatography, thin-layer chromatography and gas chromatography. A Y-isomer or an X-isomer can be separated from the ester of the formula (I) in the racemic form. However, although separation by these chromatographic techniques may be feasible in a laboratory, they are virtually impossible to carry out on an industrial scale.

SUMMARY OF THE INVENTION

With respect to α-cyano-3-phenoxybenzyl 2-(4-chlorophenyl) isovalerate, the present inventors previously found methods for obtaining a Y-isomer or a Y-isomer rich ester (see Japanese Patent Application (OPI) Nos. 103831/79 (the term "OPI" as used herein refers to a "published unexamined Japanese patent application") and 103832/79). As the result of further extensive studies on esters in which the alcohol moiety is constituted by an α-cyano-3-(4-halogenophenoxy)-benzyl alcohol, they have reached novel findings that even in the esters according to this invention which are represented by the above-described formula (I), a Y-ester is crystallized and that crystallization of a Y-ester from a "racemate" solution can be carried out by adding thereto a crystal of the Y-ester as a seed crystal. It has hitherto not been known that the Y-ester can be crystallized; still more it is a quite novel fact that the Y-ester crystal is precipitated from the "racemate" solution. As a result of further studies, the inventors have found that the presence of a basic catalyst in the crystallization system helps increase greatly the yield of the crystal of the Y-isomer, and that the Y-isomer thus obtained has a high insecticidal and/or acaricidal activity, which results in achieving the present invention.

It has also been found that a compound of the formula (I) wherein X is a fluorine atom (this compound being hereinafter referred to as "p-fluoroester") has the strongest insecticidal and/or acaricidal activity and, therefore, this compound is of great import from an economical standpoint.

Accordingly, a principal object of the present invention is to provide a mixture of stereoisomers of the ester of the formula (I) according to this invention by a very simple and easy method from an industrially obtainable racemic ester ("racemate") without applying any optical resolution and other complicated procedures. The mixture provides improved effects in controlling a variety of harmful insects and/or mites, and thus has great economic value.

DETAILED DESCRIPTION OF THE INVENTION

The mixture of stereoisomers of the ester of the formula (I) according to this invention can, for example, be obtained by the following illustrative methods.

One method comprises crystallizing a Y-isomer from a solution of an ester "racemate" of the formula (I) with or without being seeded with crystals in the presence or absence of a basic catalyst. Alternatively, the total mass of a slurry mixture containing the Y-isomer crystallized in the presence of a basic catalyst is concentrated after removal or inactivation of the catalyst, to thereby obtain a Y-isomer irch ester of the formula (I).

Illustrative methods for producing the end compound of this invention are described in detail below.

First, a Y-isomer is crystallized from a solution of a "racemate" prepared by reacting 2-(4-chlorophenyl)-isovaleric acid or a reactive derivative thereof with an α-cyano-3-(4-halogenophenoxy)benzyl alcohol or a reactive derivative thereof or reacting a 2-(4-chlorophenyl)-isovaleryl halide with an alkali metal salt of prussic acid and an α-cyano-3-(4-halogenophenoxy)-benzaldehyde, with or without being seeded with crystals in the presence or absence of a basic catalyst, followed by separation of the crystal from the mother liquor. If crystallization and separation of the crystal are effected in the absence of a basic catalyst, the ester recovered from the mother liquor which contains an increased amount of the X-isomer is brought into contact with a basic catalyst to epimerize it on the alcohol moiety. After the ratio of the X-isomer to the Y-isomer reaches an equilibrium, the crystallization is further conducted whereby the "racemate" can be converted to the Y-isomer almost quantitatively.

If crystallization of the crystal is effected in the presence of a basic catalyst, it becomes possible to obtain the crystal of the Y-isomer in an amount higher than that initially contained (usually 50%) in the "racemate". The reason is the basic catalyst causes epimerization of the asymmetric carbon atom on the alcohol moiety. As a result, the X-isomer, the content of which in the mother liquor has become greater than that in equilibrium due to crystallization of the Y-isomer, is converted to the Y-isomer, thus producing the Y-isomer in an amount higher than that initially contained. In this case, the ester present in the mother liquor may be recovered and purified for use as the starting material for the next crystallization.

Alternatively, instead of separating the mother liquor from the crystal of the Y-isomer obtained in the presence of a basic catalyst, the total mass is concentrated or subjected to other suitable means to recover the crystal of the Y-isomer together with the mother liquor, thereby yielding a Y-isomer rich ester. In this alternative method, the basic catalyst must be removed or neutralized (inactivated) following the crystallization; otherwise, the Y-isomer may possibly return to the initial "racemate" due to epimerization on the alcohol moiety.

This alternative method is more advantageous than the other methods from the industrial and economical standpoints because it permits effective use of the Y-isomer remaining in the mother liquor without losing it and is a simpler operation.

In any of the methods described above, the ratio of the X-isomer to the Y-isomer contained in the starting ester is desirably about 1:1, but in the presence of a basic catalyst, any proportion may be used. Both the acid and alcohol moieties may have any level of optical purity, and a racemic form is preferred.

It is to be emphasized that the Y-isomer rich ester of the formula (I) may be recrystallized to provide the Y-isomer of higher purity.

In the process of this invention since the ester used as the starting material is a liquid which is hardly fluid at the crystallization temperature, a solvent is generally used. Any solvent may be used without particular limitation so long as it dissolves therein the "racemate" or the X-isomer to a moderate extent and has a sufficiently low solubility to the Y-isomer. Examples of the solvent are aliphatic hydrocarbons, e.g., hexane, heptane, etc., alicyclic hydrocarbons, e.g., methylcyclohexane, etc., lower alcohols, e.g., methanol, ethanol, etc., and mixed solvents containing the same. Of these, the lower alcohols are preferred with methanol being particularly preferred. The concentration of the starting ester in the solution can be freely selected from the range of 1 to 95 wt%, preferably 20 to 80 wt%.

Crystallization of the Y-isomer is preferably performed by seeding with crystals. Examples of the seed crystals are the crystal of the Y-isomer of the corresponding ester. There is no particular limitation on the amount of the seed crystal to be used, and the use of a high amount of seed crystals generally results in rendering the crystallization well. The crystallization of the Y-isomer can be carried out continuously or semicontinuously. In this case, the seeding with crystals may be effected only at the initiation of crystallization of the Y-isomer.

Examples of the basic catalyst include nitrogencontaining bases such as ammonia, hydrazine, methylamine, ethylamine, n-propylamine, isopropylamine, n-butylamine, dimethylamine, diethylamine, di-n-propylamine, di-n-butylamine, trimethylamine, triethylamine, cyclohexylamine, ethylenediamine, ethanolamine, pyrrolidine, piperidine, morpholine, aniline, 1-naphthylamine, pyridine, quinoline, 1,5-diazabicyclo[4,3,0]-none-5-ene, etc., phosphorus-containing bases such as triphenylphosphine, tri-n-butylphosphine, etc., quaternary ammonium hydroxides such as tetramethylammonium hydroxide, tetra-n-butylammonium hydroxide, etc., metal-containing bases such as sodium hydroxide, potassium hydroxide, sodium carbonate, sodium cyanide, sodium methylate, sodium hydride, sodium amide, talc, bentonite, etc., basic ion exchange resins, and the like, with the ammonia and triethylamine being preferred.

The proportion of the catalyst to the starting ester may be freely selected from the range of from 0.001 mol% to 100 mol%, preferably from 1 mol% to 100 mol%, if the catalyst is a weak base such as nitrogen-containing and phosphorus-containing bases, etc. Strong bases such as quaternary ammonium hydroxide, sodium hydroxide, potassium hydroxide, sodium hydride, etc., are desirably used in an amount not greater than 10 mol% to prevent significant decomposition of the catalyst.

Theoretically, a crystallization temperature lower than the melting point of the desired Y-isomer may be used, but the process of this invention is generally performed at a temperature lower than the melting point by about 20° C. and preferably at −50° C. to 0° C.

The compound and the process for preparing the same according to this invention are hereunder described in greater detail by reference to the following examples which are given here for illustrative purposes only and are by no means intended to limit the invention.

In the examples, the ratio of the X-isomer to the Y-isomer was analyzed by gas chromatography.

EXAMPLE 1

700 mg of a "racemate" of a p-fluoroester (of the formula (I) wherein X is a fluorine atom) was dissolved in hexane, and the solution was adsorbed on a silica gel column (Lobor Column, Size B Lichroprep Si 60; a product of Merck Co.) and eluted with a mixed solvent of hexane and ethyl acetate (80:1 by vol. ratio). The eluate was subjected to gas chromatography to determine the ratio of the X-isomer to the Y-isomer. Fractions (Y-isomer) which were eluted later during the gas chromatograph were combined and concentrated to obtain 160 mg of the Y-isomer. The Y-isomer was stored in a refrigerator (at 0° C.) to provide a crystal having a melting point of 36° to 39° C.

EXAMPLE 2

The procedure of Example 1 was repeated to separate a Y-isomer from a "racemate" of a p-chloroester (of the formula (I) wherein X is a chlorine atom) by chromatography.

m.p.: 32° to 35° C.

EXAMPLE 3

The procedure of Example 1 was repeated to separate a Y-isomer from a "racemate" of a p-bromoester (of the formula (I) wherein X is a bromine atom) by chromatography.

m.p.: 38° to 41° C.

EXAMPLE 4

10 g of a "racemate" of a p-bromoester was dissolved in 15 g of methanol, and the solution was cooled to −19° C. To the solution were added 0.1 g of the Y-isomer crystal and 0.1 g of triethylamine, and the resulting mixture was stirred at −17° C. for 4 days. Thereafter, a mixture of 15 g of toluene and 15 g of 1% hydrochloric acid was added thereto, and the resulting mixture was stirred, followed by subjecting to phase separation. The oily layer was washed with water and concentrated to provide 9.8 g of a Y-isomer rich p-bromoester having a proportion of the X-isomer to the Y-isomer of 20:80.
$n_D^{22°} = 1.5801$

EXAMPLE 5

10 g of a p-chloroester was dissolved in 15 g of methanol, and the solution was cooled to −19° C. To the solution were added 0.1 g of the Y-isomer crystal and 0.4 cc of a 10.5% ammonia-methanol solution, and the resulting mixture was stirred at −19° C. for 7 days. The crystal was collected by filtration, washed with a small amount of cold methanol (lower than −10° C.)and vacuum-dried to provide a 6.2 g of the Y-isomer crystal having a melting point of 40.0° to 42.5° C.

EXAMPLE 6

8.09 g of a p-fluoroester was dissolved in 8.09 g of methanol and 8.09 g of heptane, and the solution was cooled to −15° C. To the solution were added 0.94 cc of an 8.4% ammonia-methanol solution and 10 mg of the Y-isomer crystal, and the resulting mixture was stirred for 3 days as it was. Thereafter, 0.26 cc of acetic acid was added to the system, and the crystal was collected by filtration, washed with 10 cc of cold heptane (−20° to −10° C.) and dried to provide 4.83 g of a crystal having a melting point of 42° to 45° C.

EXAMPLE 7

2.02 g of a p-chloroester was dissolved in 4.04 g of methanol, and the solution was cooled to −10° C. To the solution were added 10 mg of the Y-isomer crystal and 0.34 cc of an 8.4% ammonia-methanol solution, and the resulting mixture was stirred for 3 days. Thereafter, to the system were added 1 cc of 10% hydrochloric acid, 5 cc of toluene and 5 cc of water, and the system was allowed to stir at 20° to 25° C. The aqueous layer was then taken out, and the oily layer was washed twice with water and concentrated to provide 1.99 g of a Y-isomer rich p-chloroester having a proportion of the X-isomer to the Y-isomer of 30:70.
$n_D^{22.5°} = 1.5739$

EXAMPLE 8

11.2 g of a p-fluorester was dissolved in 16.8 g of methanol, and the solution was cooled to −30° C. To the solution were added 0.46 cc of triethylamine and 0.5 g of the Y-isomer crystal, and the resulting mixture was stirred for 3 days as it was. Thereafter, to the system were added 3 cc of 10% hydrochloric acid, 20 cc of water and 20 cc of toluene, and the mixture was allowed to stir at 20° to 25° C., followed by subjecting to phase separation. The thus separated oily layer was washed twice with water and concentrated to provide 10.95 g of a Y-isomer rich p-fluoroester having a proportion of the X-isomer to the Y-isomer of 18:82.
$n_D^{22.5°} = 1.5610$

EXAMPLE 9

5.0 g of a p-fluoroester was dissolved in 10.0 g of methanol, and the solution was cooled to −10° C. To the solution were added 0.58 cc of an 8.4% ammonia-methanol solution and 10 mg of the Y-isomer crystal, and the resulting mixture was stirred for 2 days. Thereafter, to the system were added 2 cc of 10% hydrochloric acid, 10 cc of toluene and 20 cc of water, and the mixture was allowed to stir at 20° to 25° C., followed by subjecting to phase separation. The thus separated oily layer was washed twice with water and concentrated to provide 9.85 g of a Y-isomer rich p-fluoroester having a proportion of the X-isomer to the Y-isomer of 32:68.
$n_D^{23°} = 1.5601$ The insecticides and/or acaricides of this invention are highly effective in controlling the below illustrated harmful insects on field crops, fruit trees, vegetables, forests and wood insanitary insects and harmful insects on livestock, exhibit a high insecticidal and/ or acaridical activity and residual activity against these harmful insects, and have low toxicity to mice, rats and other mammals. For this reason, there is no particular limitation on the field where the compound of this invention can be used with advantage.

1. Order Hemiptera white-backed planthopper, smaller brown planthopper, brown planthopper, green rice leafhopper, grain aphid, green peach aphid, cotton aphid, cabbage aphid, common green stink bug, azalea lacewing bug, citrus phitefly 2. Order Lepidoptera peach leaf miner, tea leaf roller, apple leaf miner, citrus leaf miner, diamond-back moth, summer fruit tortrix, tea tortrix, rice stem borer, grass leaf roller, corn borer, pine moth, tent caterpillar, akebia leaf-like moth, armyworm, cabbage armyworm, tobacco cutworm, smaller citrus dog 3. Order Coleoptera striped flea beetle, daikon leaf beetle, rice leaf beetle, rice plant weevil, azuki bean weevil, cupreous chafer, soybean beetle 4. Order Diptera yellow fever mosquito, anopheles, common mosquito, housefly, onion maggot, green bottle fly, flesh fly, rice leaf miner 5. Order Orthoptera short-winged rice grasshopper 6. Order Isoptera Formosan subterranean termite, Japanese termite 7. Order Blattoidea German cockroach, American cockroach, smoky brown cockroach 8. Order Acarina carmine mite, two-spotted spider mite, sugi spider mite, citrus red mite, European red mite, Japanese citrus rust mite, cyclamen mite, cattle tick The compound of this invention may be applied to the field without being combined with other ingredients, but it is more common to make a formulation of it using a carrier that facilitates handling as a controlling agent and to use the formulation after suitable dilution. Any desired formulation such as an emulsifiable concentrate, a wettable powder, a dust, a granule, a fine granule, an oil, an aerosol, a thermal fumigant (e.g., mosquito coil, an electric mosquito repellent, etc.), a spray such as fogging, a non-thermal fumigant, and poisonous bait may be made of the compound of this invention without requiring a special condition and in accordance with the method familiar to the skilled in the art of manufacture of general agrichemicals. The formulations prepared may be used in various applications depending on the purpose.

Two or more compounds of this invention may be combined to exhibit a higher insecticidal and/or acaricidal activity. The insecticidal and/or acaricidal activity of the compound of the invention may also be enhanced by mixing it with known synergists for pyrethroids, such as α-[2(2-butoxyethoxy)ethoxy]-4,5-methylenedioxy-2-propyltoluene (hereinafter referred to as piperonylbutoxide(PBO)), 1,2-methylenedioxy-4-[2-(octylsulfinyl)-propyl]benzene (hereinafter referred to as sulfoxide), 4-(3,4-methylenedioxyphenyl)-5-methyl-1,3-dioxane (hereafter referred to as safroxane), N-(2-ethylhexyl)bicyclo [2,2,1]hepta-5-ene-2,3-dicarboximide (hereinafter referred to as MGK-264), octachlorodipropyl ether (referred to as S-421), isobronyl thiocyanoacetate (hereinafter referred to as thanite), etc., and known effective synergists for allethrin and pyrethrin.

While the compound of this invention is stable against light, heat and oxidation, a stabler compound may be made by incorporating therein a suitable amount of an antioxidant, a UV absorber, or a stabilizer such as a phenol derivative, e.g., BHT or BHA, a bisphenol derivative, arylamines such as phenyl-α-naphthylamine, phenyl-β-naphthylamine, and a condensate of phenetidine and acetone, or a benzophenone compound.

Multipurpose compositions may be prepared or synergistic effect may be provided by combining the compound of this invention with other physiologically active substances such as allethrin, N-(chrysanthemoylmethyl)- 3,4,5,6-tetrahydrophthalimide (hereinafter referred to as tetramethrin), 5-benzyl-3-furylmethyl chrysanthemate (hereinafter referred to as resmethrin), 3-phenoxybenzyl chrysanthemate, 5-propargylfurfuryl chrysanthemate, and other known cyclopropane carboxylic esters and isomers thereof of pyrethrum extract, organophosphorus insecticides and acaricides such as O,O-dimethyl O-(3-methyl-4-nitrophenyl)phosphorothioate (hereinafter referred to as fenitrothion), O,O-dimethyl O-4-cyanophenylphosphorothioate (hereinafter referred to as cyanophos) and O,O-dimethyl O-(2,2-dichlorovinyl)phosphate (hereinafter referred to as dichlorovos), carbamate insecticides such as 1-naphthyl N-methylcarbamate, 3,4-dimethylphenyl N-methylcarbamate, meta-tolyl N-methylcarbamate, O-sec-butylphenyl N-methylcarbamate, O-isopropoxyphenyl N-methylcarbamate, 3-methyl-4-dimethylaminophenyl N-monomethylcarbamate and 4-dimethylamino 3,5-xylylmethylcarbamate, and other insecticides, acaricides, fungicides, nematocides, herbicides, plant growth regulators, fertilizers, pesticides against microorganisms, insect hormones and other pesticides.

The compound of this invention may be incorporated in an insecticidal and/or acaricidal composition in an amount which preferably ranges from 0.001% to 80%, more preferably from 0.01% to 50%.

The high insecticidal and/or acaricidal efficacy of the compound of this invention is hereinafter described in detail by the following illustrative formulation examples and test examples.

| Compound No. of this Invention | Structure ["X" in the formula (I)] | Example No. |
|---|---|---|
| (1) | X:F | 1 |
| (2) | X:Cl | 5 |
| (3) | X:Br | 3 |
| (4) | X:Br | 4 |
| (5) | X:F | 9 |

FORMULATION EXAMPLE 1

10 parts of each of the compounds of this invention, (1), (2), (3), (4) and (5) was mixed with 15 parts of Sorpol 3005x (a registered trademark of Toho Chemical Co., Ltd.) and 75 parts of xylene, and the mixture was thoroughly stirred to provide a 10% emulsifiable concentrate.

FORMULATION EXAMPLE 2

0.5 part of each of the compounds of this invention, (1), (2), (3), (4) and (5) was dissolved in 20 parts of acetone. To the solution was added 99.5 parts of 300 mesh clay, and the mixture was thoroughly stirred. The acetone was distilled off to provide a 0.5% dust.

FORMULATION EXAMPLE 3

0.2 part of each of the compounds of this invention, (1), (2), (3) and (4) was mixed with 2 parts of m-tolyl N-methylcarbamate and 0.3 part of PAP (isopropyl acid phosphate), and the mixture was dissolved in 20 parts of acetone. To the solution was added 97.5 parts of 300 mesh clay, and the mixture was stirred thoroughly. The acetone was distilled off to provide a 2.2% dust.

FORMULATION EXAMPLE 4

50 parts of each of the compounds of this invention, (1), (2), (3) and (4) was thoroughly mixed with Sorpol 5029-0 (special anionic surfactant). To the mixture was added 45 parts of 300 mesh diatomaceous earth, and the resulting mixture was thoroughly stirred to provide a 50% wettable powder.

FORMULATION EXAMPLE 5

10 parts of each of the compounds of this invention, (1), (2), (3) and (4) was mixed with 2.0 parts of dimethyl S-methylcarbamoylmethyl phosphorothionate. To the mixture were added 5 parts of Sorpol 3005x (described above) and 80 parts of 300 mesh diatomaceous earth. The resulting mixture was thoroughly stirred to provide a 30% wettable powder.

FORMULATION EXAMPLE 6

2 parts of each of the compounds of this invention, (1), (2), (3) and (4) was thoroughly mixed with 2 parts of sodium lignin sulfonate (binder) and 96 parts of clay (carrier) in a triturator. Water was added to the mixture with stirring in an amount of 10 wt% based on the mixture. The resulting mixture was passed through a granulator to form granules which were then air-dried to provide a 2% granule.

FORMULATION EXAMPLE 7

0.5 part of the compound (1) of this invention was dissolved in illuminating kerosine to make a total of 100 parts to provide a 0.5% oil.

FORMULATION EXAMPLE 8

A mixture of 0.5 part of the compound (2) of this invention and 2 parts of PBO (described above) was dissolved in illuminating kerosine to make a total of 100 parts to provide a 0.5% oil.

It will be demonstrated by the following test examples that the thus formulated insecticides and acaricides of this invention exhibit a high efficacy.

In the following test examples, the "racemate" (conventional product) of each of the compounds of the formula (I) was formulated in the same procedures as in each test example and then used as a reference compound.

Reference Compound
(a): a compound of the formula (I) wherein X=F
(b): a compound of the formula (I) wherein X=Cl
(c): a compound of the formula (I) wherein X=Br

TEST EXAMPLE 1

Each of the emulsifiable concentrates prepared from the compounds of this invention, (1), (2), (3), (4) and (5) in the procedures described in Formulation Example 1 was diluted with water to a predetermined concentration, and a sticker containing 20% of an alkylphenol polyethylene glycol ether and 12% of a salt of lignin sulfonic acid was added to the solution in an amount of 1 ml per 3,000 ml of the solution. Leaves of cabbage 2 months old after seeding were immersed in each solution for 1 minute. Ten 3rd instar larvae of tobacco cutworm were further immersed in each solution for 10 seconds. The leaves and cutworms were airdried and placed in each plastic cup having a diameter of 10 cm and a height of 4 cm. 48 hours later, the alive and dead was evaluated to obtain the $LC_{50}$ (median lethal concentration) (ppm).

| Compound | $LC_{50}$ (ppm) | Relative Efficacy (reference compound: 100) |
|---|---|---|
| Compound (1) | 2.1 | 238 |
| Compound (5) | 3.3 | 152 |
| Reference Compound (a) | 5.0 | 100 |
| Compound (2) | 8.1 | 188 |
| Reference Compound (b) | 15.1 | 100 |
| Compound (3) | 9.5 | 211 |
| Compound (4) | 12.0 | 167 |
| Reference Compound (c) | 20.0 | 100 |

TEST EXAMPLE 2

The compounds of this invention, (1), (2), (3) and (4) were diluted with acetone to a predetermined concentration, and 0.5 μl of each solution was topically applied to thorax of female adult CSMA-strain houseflies with a microsyringe. The flies were placed in a plastic cup having a diameter of 12 cm containing therein cotton absorbent impregnated with 3% sugar water. 24 hours later, the alive and dead was evaluated to determine the $LD_{50}$ (median lethal dose) (μg/insect).

| Compound | $LD_{50}$ (μg/insect) | Relative Efficacy (reference compound: 100) |
|---|---|---|
| Compound (1) | 0.020 | 205 |
| Reference Compound (a) | 0.041 | 100 |
| Compound (2) | 0.029 | 214 |
| Reference Compound (b) | 0.062 | 100 |
| Compound (3) | 0.040 | 200 |
| Compound (4) | 0.051 | 157 |
| Reference Compound (c) | 0.080 | 100 |

TEST EXAMPLE 3

The dusts prepared from the compounds of this invention, (1), (2), (3) and (4) in the procedures described in Formulation Example 2 were applied to rice seedlings planted in each 3 inch pot. A bell-jar duster was used to apply each dust at a pressure of 200 mmHg at a rate of 2 kg/10 ares. After the treatment, each pot was enclosed with a metal screen cage in which about 30 adult green rice leafhoppers were released. 24 hours later, the alive and dead was evaluated to found that the leafhoppers were completely killed.

TEST EXAMPLE 4

10 to 15 female adult carmine mites were placed on each leaf of potted kidney beans (2-leaf stage) 9 days old after seeding. After standing in a constant temperature room at 27° C. for a week, a lot of mites in various growth stages were observed on the beans. Each of the emulsifiable concentrates prepared from the compounds of this invention (1) and (2) in the procedures described in Formulation Example 1 was diluted 500-fold with water and applied to the beans on a turntable at a rate of 10 ml/pot. Observation 10 days later showed the mite-released kidney beans were little damaged.

While the invention has been described in detail and with reference to specific embodiments thereof, it will be apparent to one skilled in the art that various changes and modifications can be made therein without departing from the spirit and scope thereof.

What is claimed is:

1. A mixture of stereoisomers of an α-cyano-3-(4-halogenophenoxy)benzyl 2-(4-chlorophenyl)isovalerate of the formula:

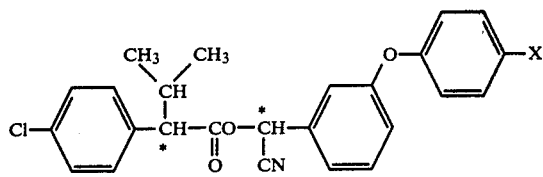

wherein X is a fluorine atom, a chlorine atom or a bromine atom, and * indicates an asymmetric carbon atom, which contains at least 60% of an enantiomer pair of a compound of said formula having an (S)-configuration on both the acid and alcohol moieties and an enantiomer thereof having an (R)-configuration on both the acid and alcohol moieties.

2. An enantiomer pair of stereoisomers of an α-cyano-3-(4-halogenophenoxy)benzyl 2-(4-chlorophenyl)-isovalerate of the formula:

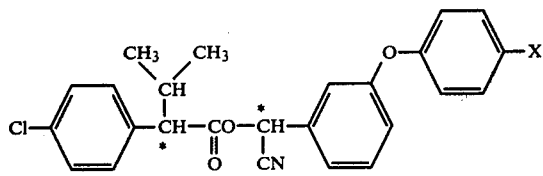

wherein X is a fluorine atom, a chlorine atom or a bromine atom, and * indicates an asymmetric carbon atom, which comprises a compound of said formula having an (S)-configuration on both the acid and alcohol moieties and an enantiomer thereof having an (R)-configuration on both the acid and alcohol moieties, and which is substantially free from other stereoisomers.

3. The mixture according to claim 1, wherein X is a fluorine atom.

4. The enantiomer pair according to claim 2, wherein X is a fluorine atom.

5. A process for preparing the enantiomer pair according to claim 2, which comprises crystallizing said enantiomer pair from a solution of the α-cyano-3-(4-halogenophenoxy)benzyl 2-(4-chlorophenyl)isovalerate with or without being seeded with crystals in the presence or absence of a basic catalyst, and separating the crystal of said enantiomer pair from the mother liquor.

6. The process according to claim 5, wherein the crystallization is carried out in the presence of a basic catalyst.

7. A process for preparing the mixture according to claim 1, which comprises crystallizing said enantiomer pair from a solution of the α-cyano-3-(4-halogenophenoxy)-benzyl 2-(4-chlorophenyl)isovalerate with or without being seeded with crystals in the presence of a basic catalyst, and recovering the crystal of said enantiomer pair together with the α-cyano-3-(4-halogenophenoxy)benzyl 2(4-chlorophenyl)isovalerate contained in the mother liquor.

8. The process according to claims 5 or 7, wherein said basic catalyst is a nitrogen-containing base.

9. The process according to claim 8, wherein said nitrogen-containing base is an ammonia or triethylamine.

10. The process according to claims 5 or 7, wherein a solvent selected from the group consisting of a lower alcohol, an aliphatic hydrocarbon, an alicyclic hydrocarbon, a mixture thereof and a solvent containing at least one of these solvents is used as a solvent for the crystallization.

11. The process according to claims 5 or 7, wherein the process is characterized by seeding with crystals.

12. The process according to claims 5 or 7, wherein the crystallization is carried out continuously or semi-continuously.

13. An insecticidal and/or acaricidal composition, which comprises as an active ingredient an insecticidally and/or acaricidally effective amount of the mixture according to claim 1.

14. A method for controlling an insect and/or mite, which comprises contacting the insect and/or mite with an insecticidally and/or acaricidally effective amount of the mixture according to claim 1.

* * * * *